(12) United States Patent
Hamm et al.

(10) Patent No.: US 7,790,397 B2
(45) Date of Patent: Sep. 7, 2010

(54) MAKING A PROGNOSIS IN CASES OF CARDIAC DISEASE USING A COMBINATION OF MARKERS

(75) Inventors: Christian Hamm, Bad Nauheim (DE); Eberhard Spanuth, Dossenheim (DE)

(73) Assignee: Roche Diagnostics, Corporation, Indianapolis, IN (US)

( * ) Notice: Subject to any disclaimer, the term of this patent is extended or adjusted under 35 U.S.C. 154(b) by 0 days.

(21) Appl. No.: 10/437,651

(22) Filed: May 14, 2003

(65) Prior Publication Data

US 2010/0173321 A1    Jul. 8, 2010

Related U.S. Application Data

(60) Provisional application No. 60/380,413, filed on May 14, 2002.

(51) Int. Cl.
*G01N 33/53* (2006.01)
(52) U.S. Cl. ......................... 435/7.1; 436/507; 436/513
(58) Field of Classification Search .................. 435/7.1, 435/7.4, 7.92, 7.93, 7.2, 7.91
See application file for complete search history.

(56) References Cited

U.S. PATENT DOCUMENTS

| | | | |
|---|---|---|---|
| 5,580,722 A | 12/1996 | Foulkes et al. | |
| 5,786,163 A | 7/1998 | Hall | |
| 6,117,644 A | 9/2000 | Debold | |
| 6,376,206 B1 | 4/2002 | Katus et al. | |
| 6,534,323 B1 | 3/2003 | Sabbadini | |
| 2003/0109420 A1 | 6/2003 | Valkirs et al. | |

FOREIGN PATENT DOCUMENTS

| | | |
|---|---|---|
| CA | 2359667 | 7/2001 |
| EP | 394819 | 4/1990 |
| WO | WO 91/09627 | 7/1991 |
| WO | WO 93/24531 | 12/1993 |
| WO | WO 00/45176 | 8/2000 |
| WO | 0223191 | 3/2002 |
| WO | 02083913 | 11/2002 |
| WO | WO02089657 | 11/2002 |
| WO | WO 2004/059293 | 7/2004 |

OTHER PUBLICATIONS

Hammerer-Lercher et al. Clinica Chimica Acta 2000, vol. 310, p. 193.*
Matsuura et al. Japanese J. Clinical Oncology 1997 vol. 27, p. 135-139.*
Liu et al. British J. Cancer 1999 vol. 79, p. 360-362.*
American Heart Association "Acute Coronary Syndrome" one page online printout.*
Christenson et al. "Cardiac troponin T and cardiac troponin I: relative values in short-term risk stratification of patients with acute coronary syndromes" (Clin. Chem. 44 (1998), 494-501).
Darbar et al. "Diagnostic Value of B-Type Natriuretic Peptide Concentrations in Patients With Acute Myocardial Infarction" (Am. J. Cardiol. 78 (1996), 284-287).
De Lemos et al. "The Prognostic Value of B=Type Natriuretic Peptide in Patients with Acute Coronary Syndromes" (New Engl. J. Med. 345 (2001), 1014-1021).
De Winter et al. "Independent prognostic value of C=reactive protein and troponin I in patients with unstable angina or non-Q-wave myocardial infarction" (Cardiovasc. Res. 42 (1999), 240-245).
De Winter et al. "C-Reactive Protein and Cardiac Troponin T in Risk Stratification: Differences in Optimal Timing of Tests Early after the Onset of Chest Pain" (Clin. Chem. 46 (2000), 1597-1603).
Eda et al. "Development of a New Microparticle-Enhanced Turbidimetric Assay for C-Reactive Protein With Superior Features in Analytical Sensitivity and Dynamic Range" (J. Clin. Lab. Anal. 12 (1998), 137-144).
Hamm et al. The Prognostic Value of Serum Troponin T in Unstable Angina (New Engl. J. Med. 327 (1992), 146-150).
Hamm et al. "Benefit of ABCIXIMAB in Patients with Refractory Unstable Angina in Relation to Serum Troponin T Levels" (New Engl. J. Med. 340 (1999), 1623-1629).
Heeschen et al. "Troponin concentrations for stratification of patients with acute coronary syndromes in relation to therapeutic efficacy of tirofiban" (The Lancet 354 (1999), 1757-1762).
Hunt et al. "Immunoreactive amino-terminal pro-brain natriuretic peptide (NT-PROBNP): a new marker of cardiac impairment" (Clin. Endocrinol. 47 (1997), 287-296).
Katus et al. "Enzyme Linked Immuno Assay of Cardiac Troponin T for the Detection of Acute Myocardial Infraction in Patients" (Mol. Cell. Cardiol. 21 (1989), 1349-1353).

(Continued)

*Primary Examiner*—Jacob Cheu
(74) *Attorney, Agent, or Firm*—McDonnell Boehnen Hulbert & Berghoff LLP

(57) ABSTRACT

The present invention concerns methods for diagnosing myocardial infarction, for performing risk stratification of myocardial infarction, for making a prognosis of a disease course in a myocardial infarction patient, for identifying a patient with elevated risk of myocardial infarction, or combinations thereof, wherein a determination of at least three markers is performed on a patient sample. Furthermore, kits for performing the methods are provided.

8 Claims, 7 Drawing Sheets

OTHER PUBLICATIONS

Klootwijk and Hamm "Acute coronary syndromes: diagnosis" (The Lancet 353, Suppl. II (1999), 10-15).
Kuller et al. "Relation of C-Reactive Protein and Coronary Heart Disease in the MRFIT Nested Case-Control Study" (Am. J. Epidem. 144 (1996), 537-547).
Luizzo et al. "The Prognostic Value of C-Reactive Protein and Serum Amyloid A Protein in Severe Unstable Angina" (N. Engl. J. Med. 331 (1994), 417-424).
Ohman et al. Cardiac Troponin T Levels for Risk Stratification in Acute Myocardial Ischemia (N. Engl. J. Med. 335 (1996), 1333-1334).
Price et al. Development and validation of a particle-enhanced turbidimetric immunoassay for C-reactive protein (J. Immunol. Methods. 99 (1987), 205-211).
Richards et al. Plasma N-Terminal Pro-Brain Natriuretic Peptide and Adrenomedullin (Circulation 97 (1998), 1921-1929).
Struthers "How to use natriuretic peptide levels for diagnosis and prognosis" (Eur. Heart J. 20 (1999), 1374-1375).
Talwar et al. "Plasma N-terminal pro-brain natriuretic peptide and the ECG in the assessment of left-ventricular systolic dysfunction in a high risk population" (Eur. Heart J. 20 (1999), 1736-1744).
Wei et al. "Natriuretic Peptide System in Human Heart Failure" (Circulation 88 (1993), 1004-1009).
Mair, et al., "The Impact of Cardiac Natriuretic Peptide Determination on the Diagnosis and Management of Heart Failure", *Clinical Chemistry and Laboratory Medicine*, 39(7):571-588, 2001.
Sabatine, et al., "Multimarker Approach to Risk Stratification in Non-ST Elevation Acute Coronary Syndromes", *Curculation*, vol. 105, No. 15, pp. 1760-1763, 2002.
International Search Report dated Dec. 17, 2003.
Panteghini, "Recommendations on Use of Biochemical Markers in Acute Coronary Syndrome: IFCC Proposals", The Journal of the International Federation of Clinical Chemistry and Laboratory Science, vol. 13, No. 2.
Palazzuoli, et al., "Brain Natriuretic Peptide and Other Risk Markers for Outcome Assessment in Patients with Non-ST-Elevation Coronary Syndromes and Preserved Systolic Function", The American Journal of Cardiology, p. 1322-1328 (2006).
Lacour, et al., "Procalcitonin, IL-6, IL-8, 1L-1 receptor antagonist and C-reactive protein as identificators of serious bacterial infections in children with fever without localising signs", Eur. J. Pediatr (2001) 160:95-100.
Sakhuja, et al., "NT-proBNP—A New Test for Diagnosis, Prognosis and Management of Congestive Heart Failure", US Cardiology, p. 148-149 (2004).
Mueller, et al., "Long-term stability of endogenous B-type natriuretic peptide (BNP) and amino terminal proBNP (NT-proBNP) in frozen plasma samples", Clin. Chem. Lab. Med. 2004;42(8):942-944 (2004).
Mueller, et al., "Head-to-Head comparison of the diagnostic utility of BNP and NT-proBNP in symptomatic and asymptomatic structural heart disease", Clinica Chimica Acta 341 (2004) 41-48.
Liu, et al., "Circulating intercellular adhesion molecule 1 (ICAM-1), E-selectin and vascular cell adhesion molecule 1 (VCAM-1) in head and neck cancer", British Journal of Cancer (1999) 78(2):360-362.
Matsuura, et al., "Increased Level of Circulating Adhesion Molecules in the Sera of Breast Cancer Patients with Distant Metastases", Jpn J Clin Oncol 1997;27(3)135-139.
Hartmann, et al., "High Altitude Increases Circulating Interleukin-6, Interleukin-1 Receptor Antagonist and C-Reactive Protein", Cytokln, vol. 12, No. 3 (2000) pp. 246-252.
Taaffe, et al , "Cross-sectional and Prospective Relationships of Interleukin-6 and C-Reactive Protein with Physical Performance in Elderly Persons: MacArthur Studies of Successful Aging", Journal of Gerontology: Medical Services, 2000 vol. 55A, No. 12, M709-M715.
Fischer, et al., "Effects of Sevoflurane and Propofol on Procalcitonin and C-Reactive Protein Concentrations in Patients Undergoing Off-Pump Coronary Artery Bypass Graft Surgery", Anesthesiology 2002; 96: A155.

Abrams, "C-reactive protein, inflammation, and coronary risk: an update", Cardiol Clin 21 (2003) 327-331.
Rallidis, et al., "Dietary α-linolenic acid decreases C-reactive protein, serum amyloid A and interleukin-6 in dyslipidaemic patients", Atherosclerosis 167 (2003) 237-242.
Blake, et al., "C-Reactive Protein and Other Inflammatory Risk Markers in Acute Coronary Syndromes", Journal of the American College of Cardiology, (2003) 41(4):S37-42.
O'Neil, et al , "Cardiac Markers Protocols in a Chest Pain Observation Unit", Emerg. Med. Clin. North Am. (2001) 19:67.
Lindahl, "Markers of myocardial damage in acute coronary syndromes—therapeutic implications", Clinca Chimica Acta 311 (2001) 27-32.
Antmann, "Decision Making with Cardiac Troponin Tests", N. Engl. J. Med. vol. 346, No. 26 (2002) 2079.
Sarko, et al. "Cardiac Troponins", The Journal of Emergency Medicine, vol. 23, No. 1, pp. 57-65(2002).
Williams, et al , "Recommended standards for biochemical markers for myocardial damage" All Wales Clinical Biochemistry Audit Group, Ann. Clin. Biochem. (2005) 42:346-350.
Foote, et al., "Detection of Exercise-Induced Ischemia by Changes in B-Type Natriuretic Peptides", Journal of the American College of Cardiology, vol. 44, No. 10 (2004).
Apple, et al., "Multi-Biomarker Risk Stratification of N-Terminal Pro-B-Type Natriuretic Peptide, High-Sensitivity C-Reactive Protein, and Cardiac Troponin T and I in End-Stage Renal Disease for All-Cause Death", Clinical Chemistry. 50:12, 2279-2285 (2004).
Chapelle, "Multimarker Approach to Risk Stratification", Clin. Chem. Lab. Med. 41 (10), A79, abstract No. S11.3.
Lindahl, "Diagnosis and Management of Patients with Suspected Acute Myocardial Infarction", Scand J Clin Lab Invest 2005; 65 (Suppl 240):93-98.
Mueller, et al , "Biochemical diagnosis of impaired left ventricular ejection fraction—comparison of the diagnostic accuracy of brain natriuretic peptide (BNP) and amino terminal proBNP (NT-proBNP)", Clin Chem Lab Med 2004;42(2):159-163.
James, et al., "(Prognosis in unstable coronary artery disease. Multimarker strategy is the best basis for the therapeutic choice). English translation of title", Läkartidningen, 101 (17), 1514-1519 (2004) Abstract Only.
Wu, et al., "The ischemia-modified albumin biomarker for myocardial ischemia", Medical Laboratory Observer, 36:36-38; 40 (2003).
Pentilla, et al., "Myoglobin, creatine kinase MB isoforms and creatine kinase MB mass in early diagnosis of myocardial infarction in patients with acute chest pain", Clin. Biochem. 33:647-653 (2002).
Heeschen, et al., "Soluble CD40 Ligand in Acute Coronary Syndromes", New England J. Medicine, 348:1104-111 (2003).
Guidelines for Risk Stratification After Myocardial Infarction, Annals of Internal Medicine, 126:556-582 (1997).
Doukky, et al., "Risk Stratification in Patients with Unstable Angina and Non-ST Segment Elevation Mycardial Infarction: Evidence-Based Review", Journal of Invasive Cardiology, 14(4):215-220 and 254-262.
Sabatine, et al., "Multimarker Approach to Risk Stratification in Non-ST Elevation Acute Coronary Syndromes", Circulation, 105:1760-1763 (2002).
Omland, et al., "Prognostic Value of N-terminal Pro-Atrial and Pro-Brain Natriuretic Peptide in Patients with Acute Coronary Syndromes", Am. J. Cardiology, 89:463-465 (2002).
"Acute Coronary Syndrome", Excerpt from the webpage of the American Heart Association, downloadable from http://www.americanheart.org/presenterjhtml?identifier=3010002 downloaded Feb. 1, 2007.
"Myocardial ischemia, injury and infarction", Excerpt from the webpage of the American Heart Association, downloadable from http://www.americanheart.org/presenterjhtml?identifer=251downloaded Feb. 1, 2007.
Pemberton, et al., "Deconvulution Analysis of Cardiac Natriuretic Peptides During Actue Volume Overload", Hypertension 36(3):355-359 (2000).
Richards, et al., "Plasma N-Terminal Pro-Brain Natriuretic Peptide and Adrenomedullin", Circulation, 97:1921-1929 (1998).

Clerico, "Pathophysiological and Clinical Relevance of Circulating Levels of Cardiac Natriuretic Hormones: Are They Merely Markers of Cardiac Disease?", Clin. Chem. Lab. Med, 40(8):752-760 (2002).

Clerico et al., "Clinical relevance of cardia natriuretic peptides measured by means of competitive and non-competitive immunoassay methods in patients with renal failure on chronic hemodialysis", J. Enndocrinol. 24:24-30 (2001) (Abstract only).

Campbell et al., "Plasma Amino-Terminal Pro-Brain Natriuretic Peptide: A Novel Approach to the Diagnosis of Cardiac Dysfunction" Journal of Cardiac Failure, vol. 6, No. 2, pp. 130-139 (2000).

Antman et al., "Cardiac-Specific Troponin I Levels to Predict the Risk of Mortality in Patients with Acute Coronary Syndromes", N. Engl. J. Med. 335:1342-1349 (1996).

De Lemos et al., "The Prognostic Value of B-Type natriuretic Peptide in Patients with Acute Coronary Syndromes", The New England Journal of Medicine, vol. 345, No. 14, pp. 1014-1020 (2001).

Biasucci et al., "Elevated Levels of C-Reactive Protein at Discharge in Patients with Unstable Angina Predict Recurrent Instability", Circulation, 99:855-860 (1990).

Omland et al., "N-Terminal Pro-B-type Natriuretic Peptide and Long-Term Mortality in Acute Coronary Syndromes", Circulation, 106:2913-18 (2002).

Hunt et al., "Immunoreactive amino-terminal pro-brain natriuretic peptide (NT-PROBNP): a New Marker of Cardiac Impairment", Clincial Endocrinology, 47. 287-296 (1997).

Luc et al., "C-Reactive Protein, Interleukin-6, and Fibrinogen as Predictors of Coronary Heart Disease", Arterioscler. Thrmob. Vasc. Biol. 23:1255-1261 (2003).

Gaini et al., "Procalcitonin, lipopolysaccharide-binding protein, interleukin-6 and C-reactive protein in community-acquired infections and sepsis: a prospective study", Critical Care 10 (2) R53 (2006).

Jiang et al., "Serum Interleukin-6, Tumor Necrosis Factorα and C-reactive Protein in Early Predictionof Severity of Acute Pancreatitis", J. Chin. Med. Assoc., 67:442-446 (2004).

Labarrere et al., "Interleukin-6, C-reactive protein and transplant coronary artery disease", Experimental Biology/IUPS 2005: Meeting Abstracts A1515 (2005).

Morrow, et al., "Prognostic Value of Serial B-Type Natriuretic Peptide Testing During Follow-up of Patients with Unstable Coronary Artery Disease", JAMA, vol. 294, No. 22 (2005).

Packard, et al., "Inflammation in Atherosclerosis: From Vascular Biology to Biomarker Discovery and Risk Prediction", Clinical Chemistry, 54:1, p. 24-38 (2008).

De Lemos, et al., "The Prognostic Value of B-Type Natriuretic Peptide in Patients with Acute Coronary Syndromes", The New England Journal of Medicine, vol. 345, No. 14, p. 1014-1021 (2001).

Jernberg, et al., "N-Terminal Pro Brain Natriuretic Peptide on Admission for Early Risk Stratification of Patients with Chest Pain and No ST-Segment Elevation", Journal of the American College of Cardiology, vol. 40, No. 3, p. 437-445 (2002).

Morrow, et al., "Evaluation of B-Type Natriuretic Peptide for Risk Assessment in Unstable Angina/Non-ST-Elevation Myocardial Infarction", Journal of the American College of Cardiology, vol. 41, No. 8, p. 1264-1272 (2003).

Lindahl, et al., "Serial Analyses of N-Terminal Pro-B-Type Natriuretic Peptide in Patients with Non-ST-Segment Elevation Acute Coronary Syndromes", Journal of the American College of Cardiology, vol. 45, No. 4, p. 533-541 (2005).

Weber, et al., "N-Terminal B-Type Natriuretic Peptide Assessment Provides Incremental Prognostic Information in Patients with Acute Coronary Syndromes and Normal Troponin T Values Upon Admission", Journal of the American College of Cardiology, vol. 51, No. 12, p. 1188-1195 (2008).

James, et al., "N-Terminal Pro-Brain Natriuretic Peptide and Other Risk Markers for the Separate Prediction of Mortality and Subsequent Myocardial Infarction in Patients with Unstable Coronary Artery Disease", Circulation, p. 275-281 (2003).

Pai, et al., "Inflammatory Markers in the Risk of Coronary Heart Disease in Men and Women", The New England Journal of Medicine, 351:25, p. 2599-2610 (2004).

Yamaguchi, et al., "Impact of Serum Insulin-like Growth Factor-1 on Early Prognosis in Acute Myocardial Infarction", Internal Medicine, 47:819-825 (2008).

Heeschen, et al., "N-terminal Pro-B-Type Natriuretic Peptide Levels for Dynamic Risk Stratification of Patients with Acute Coronary Syndromes", Circulation, p. 1-7 (2004).

Pedersen, et al., "Urinary Albumin Excretion and its Relationship to C-reactive Protein and Proinflammatory Cytokines in Patients with Cancer and Febrile Neutropenia", Scandinavian Journal of Infectious Diseases, 35:8, 491-494 (2003).

Segev, et al., "Pre-procedural plasma levels of C-reactive protein and interleukin-6 do not predict late coronary angiographic restenosis after elective stenting", European Heart Journal, 25, p. 1029-1035 (2004).

Saleh, et al., "Stent implantation, but not pathogen burden, is associated with plasma C-reactive protein and interleukin-6 levels after precutaneous coronary intervention in patients with stable angina pectoris", American Heart Journal, vol. 149, No. 5, p. 876-882 (2005).

Eda, et al., "Development of a new Microparticle-Enhanced Turbidimetric Assay for C-Reactive Protein with Superior Features in Analytical Sensitivity and Dynamic Range", Journal of Clinical Laboratory Analysis, 12:137-144 (1998).

Liuzzo, et al., "The Prognostic Value of C-Reactive Protein and Serum Amyloid a Protein in Severe Unstable Angina", The New England Journal of Medicine, vol. 331, No. 7, p. 417-424 (1994).

Eilertsen, et al., "The effects of oral and transdermal hormone replacement therapy on C-reactive protein levels and other inflammatory markers in women with a high risk of thrombosis", Maturitas, vol. 52, No. 2, p. 111-118 (2005), abstract only.

Bluher, et al., "Association of interleukin-6, C-reactive protein, interleukin-10 and adiponectin plasma concentrations with measures of obesity, insulin sensitivity and glucose metabolism", Exp. Clin. endocrinol. Diabetes, 113:9(534-537 (2005) abstract only.

Ilhan, et al., "Procalcitonin, c-reactive protein and neopterin levels in patients with coronary atherosclerosis", Acta. Cardiologica., vol. 60, No. 4, p. 361-365 (2005) abstract only.

Tzoulaki, et al., "C-reactive protein, interleukin-6, and soluble adhesion molecules as predictors of progressive peripheral atherosclerosis in the general population", Circulation, vol. 112, No. 7, p. 976-983 (2005) abstract only.

Piche, et al., "Relation of high-sensitivity C-reactive protein, interleukin-6, tumor necrosis factor-alpha, and fibrinogen to abdominal adipose tissue, blood pressure, and cholesterol and triglyceride levels in healthy postmenopausal women", American Journal of Cardiology, vol. 96, No. 1, p. 92-97 (2005) abstract only.

Kasapis, et al., "The effects of physical activity on serum C-reactive protein and inflammatory markers—A systematic review", Journal of the American College of Cardiology, vol. 45, No. 10, p. 1563-1569 (2005) abstract only.

Hoshi, et al., "Relations of serum high-sensitivity C-reactive protein and interleukin-6 levels with silent brain infarction", Stroke, vol. 36, No. 4, p. 768-772 (2005) abstract only.

Nomoto, et al., "Involvement of inflammation in acute coronary syndromes assessed by levels of high-sensitivity C-reactive protein, matrix metalloproteinase-9 and soluble vascular-cell adhesion molecule-1", Journal of Cardiology, 45:5(201-206) (2003) abstract only.

Mitani, et al., "Elevate levels of high-sensitivity C-reactive protein and serum amyloid-A late after Kawasaki disease—Association between inflammation and late coronary sequelae in Kawasaki disease", Circulation, vol. 111, No. 1, p. 38-43 (2005) abstract only.

Dosa, et al., "Marked decrease in the levels of two inflammatory markers, hs-C-reactive protein and fibrinogen in patients with severe carotid atherosclerosis after eversion carotid endarterectomy", Inflammation Research, vol. 53, No. 11 (2004) abstract only.

Khaodhiar, et al., "Serum levels of interluekin-6 and C-reactive protein correlate with body mass index across the broad range of obesity", Journal of Parenteral and Enteral Nutrition, vol. 28, No. 6, p. 410-475 (2004) abstract only.

Bautista, et al., "Independent association between inflammatory markers (C-reactive protein), interleukin-6, and TNF-(alpha)) and essential hypertension" Journal of Human Hypertension 19:2(149-154), (2005) abstract only.

Bogaty, et al., "Impact of prolonged cyclooxygenase-2 inhibition on inflammatory markers and endothelial function in patients with ischemic heart disease and raised C-reactive protein—A randomized placebo-controlled study", Circulation, vol. 110, No. 8, p. 934-939 (2004) abstract only.

Sondergaard, et al., "The inflammatory markers C-reactive protein and serum amyloid A in refugees with and without posttraumatic stress disorder," Clinica Chimia Acta, vol. 324, No. 1-2, p. 93-92 (2004) abstract only.

Maier, et al., "Inflammatory markers at the site of ruptured plaque in acute myocardial infarction: locally increased interleukin-6 and serum amyloid A but decreased C-reactive protein", European Heart Journal, vol. 25, p. 450 (2004) abstract only.

Danesh, et al., "C-reactive protein and other circulating markers of inflammation in the prediction of coronary heart disease", New England Journal of Medicine, vol. 350, No. 14, p. 1387-1397 (2004) abstract only.

Chapman, et al., "Monocyte count, but not C-reactive protein or interleukin-6, is an independent risk marker for subclinical carotid atherosclerosis", Stroke, vol. 35, No. 7, p. 1619-1624 (2004) abstract only.

Libby, et al., "Inflammation and atherosclerosis: Role of C-reactive protein in risk assessment", American Journal of Medicine, vol. 1169, No. Suppl. 6A, p. 9-16 (2004) abstract only.

Doo, et al., "Associations among oxidized low-density lipoprotein antibody, C-reactive protein, interleukin-6, and circulating cell adhesion molecules in patients with unstable angina pectoris", American Journal of Cardiology, vol. 93, No. 5, p. 554-558 (2004) abstract only.

Luc, et al., "C-reactive protein, interleukin-6, and fibrinogen as predicators of coronary heart disease the PRIME study", Arteriosclerosis Thrombosis and Vascular Biology, vol. 23, No. 7, p. 1255-1561 (2003) abstract only.

Rallidis, et al., "Dietary alpha-linolenic acid decreases C-reactive protein, serum amyloid A and interleukin-6 in dyslipidaemic patients", Atherosclerosis, vol. 167, No. 2, p. 237-242 (2003) abstract only.

Blake, et al., "C-reactive protein and other inflammatory risk markers in acute coronary syndromes", Journal of the American College of Cardiology, vol. 41, No. 4 supp. S, p. 37S-42S (2003) abstract only.

Abrams, "C-reactive protein, inflammation, and coronary risk: An update", Cardiology Clinics, 21:3(327-331), (2003) abstract only.

Fischer, et al., "Effects of Sevoflurane and Propofol on Procalcitonin and C-Reactive Protein Concentrations in Patients Undergoing Off-Pump Coronary Artery Bypass Graft Surgery", Anesthesiology Abstracts of Scientific Papers Annual Meeting, No. 2, Abstract No. A-155 (2002) abstract only.

Sasaki, et al., "Differentiating between bacterial and viral infection by measuring both C-reactive protein and 2'-5'-oligoadenylate synthetase as inflammatory markers", Journal of Infection and Chemotherapy, vol. 8, No. 1, p. 76-80 (2002) abstract only.

Boylan, et al., "Interferon-beta1a administration results in a transient increase of serum amyloid A protein and C-reactive protein: Comparison with other markers of inflammation", Immunology Letters, vol. 75, No. 3, p. 191-197 (2001) abstract only.

Lacour, et al., "Procalcitonin, IL-6, IL-8, IL-1 receptor antagonist and C-reactive protein as identificators of serious bacterial infections in children with fever without localising signs", European Journal of Pediatrics, vol. 160, No. 2, p. 95-100 (2001) abstract only.

Hartmann, et al., "High altitude increases circulating interleukin-6, interleukin-1 receptor antagonist and C-reactive protein", Cytokine, vol. 12, No. 3, p. 246-252 (2000) abstract only.

Taaffe, et al., "Cross-sectional and prospective relationships of interleukin-6 and c-reactive protein with physical performance in elderly persons: Mac Arthur studies of successful aging", Journal of Gerontology, 52:12(M709-M715) (2000) abstract only.

Mulvihill, et al., "Inflammatory markers in acute ischaemic syndromes: Soluble vascular cell adhesion molecule-1 versus C-reactive protein", Circulation, vol. 100, No. 18 suppl., p. I.372 (1999) abstract only.

* cited by examiner

MAKING A PROGNOSIS IN CASES OF CARDIAC DISEASE USING A COMBINATION OF MARKERS

PRIORITY

This application claims the benefit of U.S. Provisional application 60/380,413 filed May 14, 2002, which is incorporated herein in its entirety.

BACKGROUND

A number of markers are used in the diagnosis of coronary diseases such as NSTEMI and acute coronary syndrome, e.g., troponin T, C-reactive protein (CRP) and brain-natriuretic peptide (BNP). The elevation of the concentration of one of these markers is associated with an elevation in the likelihood of ischemic events, including death. This is described, for example, in the publications Hamm et al. (New Engl. J. Med. 327 (1992), 146-150), Hamm et al. (New Engl. J. Med. 340 (1999), 1823-1629, Heeschen et al. (The Lancet 354 (1999), 1757-1962), Klootwijk and Hamm (The Lancet 353, Suppl. II (1999), 10-15), Wei et al. (Circulation 88 (1993), 1004-1009), De Lemos (New Engl. J. Med. 345 (2001), 1014-1021). In De Winter et al. (Cardiovasc. Res. 42 (1999), 240-245) and De Winter et al. (Clin. Chem. 46 (2000), 1597-1603). CRP and troponin I or troponin T are two independent markers for the risk stratification of patients with acute coronary syndrome.

The disadvantage of diagnostic procedures using one or two markers, is that all high-risk patients are not successfully identified. Therefore methods for diagnosing myocardial infarction and/or for risk stratification of acute coronary syndrome that have improved identification of high-risk patients is needed in the art.

SUMMARY OF THE INVENTION

Figure 1:
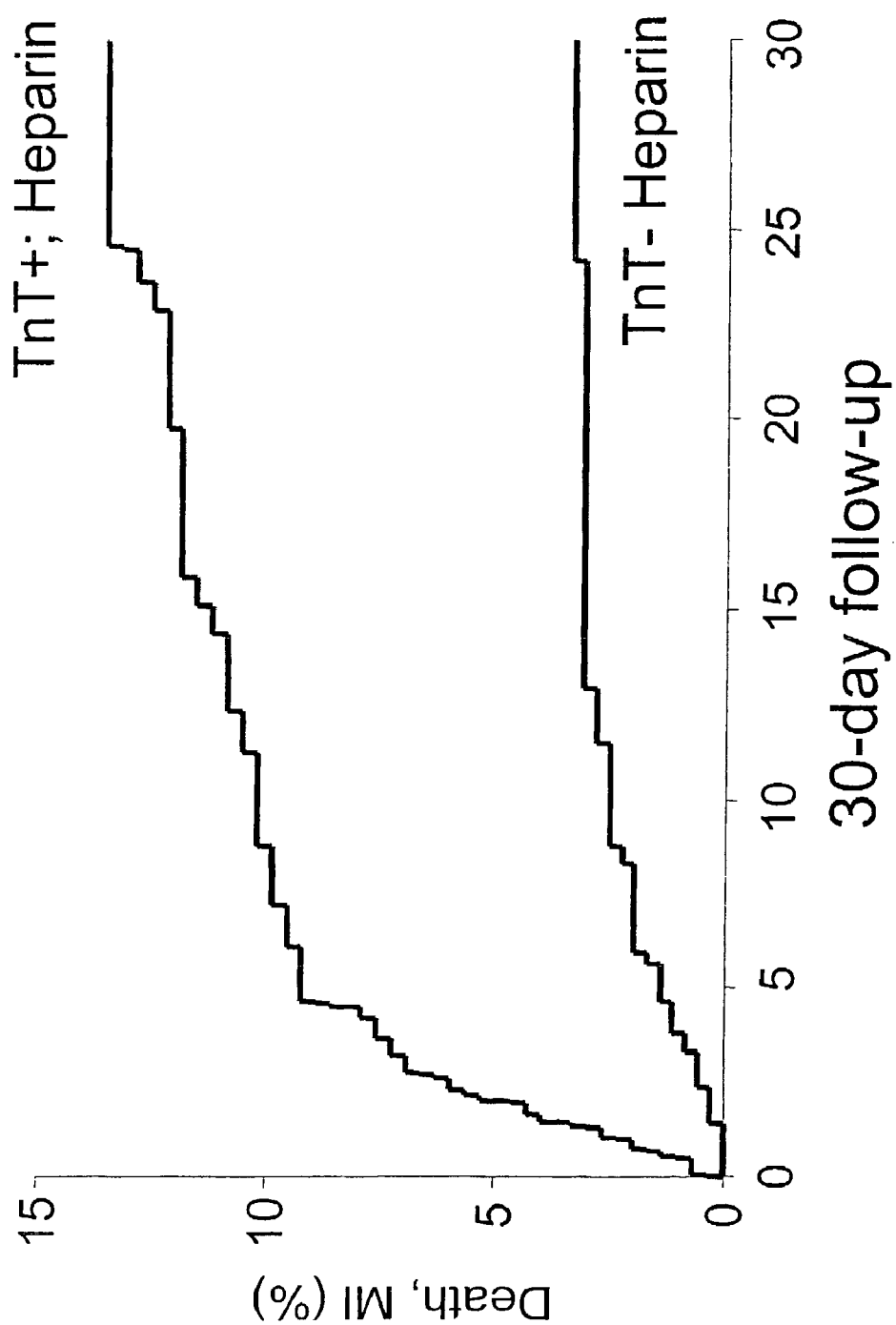
FIG. 1 shows the curve for troponin T (TnT) assays carried out on 500 patients with acute coronary syndrome (NSTEMI).

The present invention concerns methods and compositions for diagnosing myocardial infarction, in particular, Non-ST-Elevation Myocardial Infarction (NSTEMI), for risk stratification of the acute coronary syndrome, for determining presence or absence of elevated risk of myocardial infarction, for determining the prognosis of a patient with myocardial infarction, or a combination thereof whereby a determination of at least three markers is performed on a patient to be investigated. Furthermore, kits for performing methods of the invention are provided.

One embodiment of the invention provides a method for diagnosing myocardial infarction, for performing risk stratification of myocardial infarction, or both. The method comprises determining the presence, quantity, or both presence and quantity of at least three markers in a patient sample, wherein the at least three markers comprise at least one neurohormonal marker, at least one ischemic marker, and at least one inflammatory marker. Myocardial infarction is diagnosed or risk stratification is performed by the method. The neurohormonal marker can be selected from the group consisting of A-type natriuretic peptide (ANP), N-terminal fragment of pro-ANP (NT-ProANP), and B-type natriuretic peptide (BNP). The ischemic marker can be selected from the group consisting of troponin T and troponin I. The inflammatory marker can be selected from the group consisting of C-reactive protein (CRP), interleukin, and an adhesion molecule. The inflammatory marker can also be selected from the group consisting of IL-6, endothelial intercellular adhesion molecule (ICAM), and vascular adhesion molecule (VCAM). The presence, quantity, or both presence and quantity of the markers can be determined in parallel, can be determined on an automated analyzer, and can be determined using a rapid assay. A single patient sample can be used.

Another embodiment of the invention provides a method for identifying a patient with elevated risk of myocardial infarction. The method comprises determining the presence, quantity, or both presence and quantity of at least three markers in a patient sample. The at least three markers comprise at least one neurohormonal marker, at least one ischemic marker, and at least one inflammatory marker. A patient with elevated risk of acute myocardial infarction is identified using the method.

Yet another embodiment of the invention provides a method for making a prognosis of a disease course in a myocardial infarction patient. The method comprises determining the presence, quantity, or both presence and quantity of at least three markers in a patient sample. The at least three markers comprise at least one neurohormonal marker, at least one ischemic marker, and at least one inflammatory marker. A prognosis is made using the method.

Still another embodiment of the invention provides a reagent kit for diagnosing myocardial infarction, for performing risk stratification of myocardial infarction, for making a prognosis of a disease course in a myocardial infarction patient, for identifying a patient with elevated risk of myocardial infarction, or combinations thereof. The kit comprises at least one detection reagent for a neurohormonal marker, at least one detection reagent for an ischemic marker, and at least one detection reagent for an inflammatory marker.

DETAILED DESCRIPTION

Methods of the invention comprise determining the presence, quantity, or both presence and quantity of at least three markers in a patient sample, wherein at least one neurohormonal marker, at least one ischemic marker, and at least one inflammatory marker.

Surprisingly it has been found that neurohormonal markers, ischemic markers, and inflammatory markers represent three groups of independent risk indicators, so that, by combining these three marker groups according to the invention, an additively increased sensitivity and specificity is obtained. Therefore, higher predictive values and a higher diagnostic effectiveness are possible, especially in patients with elevated risk and/or an unfavorable prognosis. Methods and compositions of the invention are useful for, e.g., diagnosing myocardial infarction, including acute myocardial infarction, and for performing risk stratification of myocardial infarction, including acute myocardial infarction. Risk stratification is the quantification of a patient's overall short term and long term risk. See e.g., Guidelines for Risk Stratification after myocardial Infarction, Ann. Intern. Med. 126:556-582 (Parts I and II) (1997); Doukky & Calvin, Risk Stratification in patients with unstable angina and non-ST segment elevation myocardial infarction: evidence-based review (Parts I and II), J. Invasive Cardiol., 14(4):215-220 and 254-262. Methods and compositions of the invention can also be used to identify patients with elevated risk of myocardial infarction, including acute myocardial infarction, and prognosis of a disease course in an acute myocardial infarction patient, including acute myocardial infarction patients. The methods and compositions of the invention thus make it possible to establish an improved indication for suitable therapeutic measures.

When cardiac disease is present, in particular Non-ST-elevation myocardial infarction (NSTEMI), a higher number of patients with elevated risk and/or an unfavorable prognosis can be identified and handled adequately with the methods and compositions of the invention than with current diagnostic procedures that include the determination of individual markers. As a result of the combination of three different markers in making a diagnosis, the frequency of cases of death and other cardial complications can be further reduced.

Methods according to the invention comprise the determination of at least three markers, whereby at least one neurohormonal marker, at least one ischemic marker, and at least one inflammatory marker are determined.

A neurohormonal marker can be selected, for example, from atrial (A-type) natriuretic peptide (ANP), brain (B-type) natriuretic peptide (BNP), or N-terminal fragments of propeptides NT-ProANP and NT-ProBNP. ProBNP is a preferred neurohormonal marker.

Troponin T or troponin I, for example, can be ischemic markers.

An inflammatory marker can be selected, for example, from C-reactive protein (CRP), interleukins, particularly IL-6, and adhesion molecules such as VCAM and ICAM.

Determination of the presence, quantity or both presence and quantity of markers can be performed, for example, in parallel or multiple samples in one or more samples from a patient to be investigated. One or more samples collected from a patient, e.g., blood, serum, or plasma samples, are investigated in one or more tests simultaneously or immediately sequentially. The determinations can be performed on a single patient sample from the same patient.

Determination of the presence, quantity or both presence and quantity of markers can be performed, for example using any commercial assay. Automated analyzers can be used for the determination. As an alternative, rapid assays, e.g., for use in an emergency room, hospital ward, intensive care station, ambulance, or doctor's office, or as a patient self-test can also be used.

Determination of markers can be done using, for example, an immunoassay employing antibodies directed against the marker. Detection of C-reactive protein as an inflammatory marker, can be accomplished as described by, for example, Liuzzo et al. (N. Engl. J. Med. 331 (1994), 417-424), Kuller et al. (Am. J. Epidem. 144 (1996), 537-547), Price et al. (J. Immunol. Methods. 99 (1987), 205-211) or Eda et al. (J. Clin. Lab. Anal. 12 (1998)), 137-144). An example of a test for detection of C-reactive protein is an immunoturbidimetric test, e.g., the Tina-Quant®-Test from Roche Diagnostics GmbH, Mannheim.

The detection of BNP or NT-ProBNP as neurohormonal markers is described, for example, in Richards et al. (Circulation 97 (1998), 1921-1929), Struthers (Eur. Heart J. 20 (1999), 1374-1375), Hunt et al. (Clin. Endocrinol. 47 (1997), 287-296), Talwar et al. (Eur. Heart J. 20 (1999), 1736-1744), Darbar et al. (Am. J. Cardiol. 78 (1996), 284-287) and in EP-A-0 648 228 and WO 00/45176. An example of a test is an electrochemiluminescence immunoassay, e.g., the electrochemiluminescence immunoassy (ECLIA) test format from Roche Diagnostics GmbH, Mannheim.

Troponin T, as an example of an ischemic marker, can be determined as described in, for example, to Katus et al. (Mol. Cell. Cardiol. 21 (1989), 1349-1353), Hamm et al. (N. Engl. J. Med 327 (1992), 146-150), Ohmann et al. (N. Engl. J. Med. 335 (1996), 1333-1334), Christenson et al. (Clin. Chem. 44 (1998), 494-501) and numerous other publications, and to EP-A-0 394 819. Tests for the detection of troponin T include, for example, electrochemiluminescence immunoassays, e.g., the Elecsys® Troponin-T and Elecsys® Troponin T STAT test formats from Roche Diagnostics GmbH, Mannheim.

Compositions of the invention include reagent kits for diagnosing acute coronary syndrome. A kit contains detection reagents for determining the presence, quantity, or both presence and quantity of at least three markers. The kit comprises at least one detection reagent for a neurohormonal marker at least one detection reagent for an ischemic marker, and at least one detection reagent for an inflammatory marker.

A reagent kit can be designed so that the reagents are adapted for performing parallel determinations of markers and, in particular, for performing determinations on a single patient sample. Detection reagents can be used that make it possible to determine all three markers using a single test format, e.g., an Enzymun-Test®, an electrochemiluminescence test, a turbidimetric test, or a rapid assay on a test strip.

A reagent kit can be used, e.g., to identify patients with acute coronary syndrome that have an elevated risk and/or an unfavorable prognosis. A reagent kit can be designed so that the reagents are adapted for performing determinations on an automated analyzer or a rapid assay.

The invention shall be explained further by the following non-limiting examples. All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Investigations of three markers troponin T, NT-ProBNP and CRP were carried out on 500 patients with acute coronary syndrome (NSTEMI). Troponin T STAT-Tests from Roche Diagnostics GmbH, Mannheim were used to determine troponin T. The Tina-Quant® CRP Tests from Roche Diagnostics GmbH, Mannheim were used to determine CRP, and ECLIA Tests from Roche Diagnostics, Mannheim were used to determine NT-ProBNP. Each test was performed according to the manufacturer's instructions.

All three parameters differentiate between patients with unfavorable 30-day diagnosis with regard for death and myocardial infarction and patients with 30 event-free days.

FIG. 1 shows the curve for troponin T (TnT)

Figure 2:
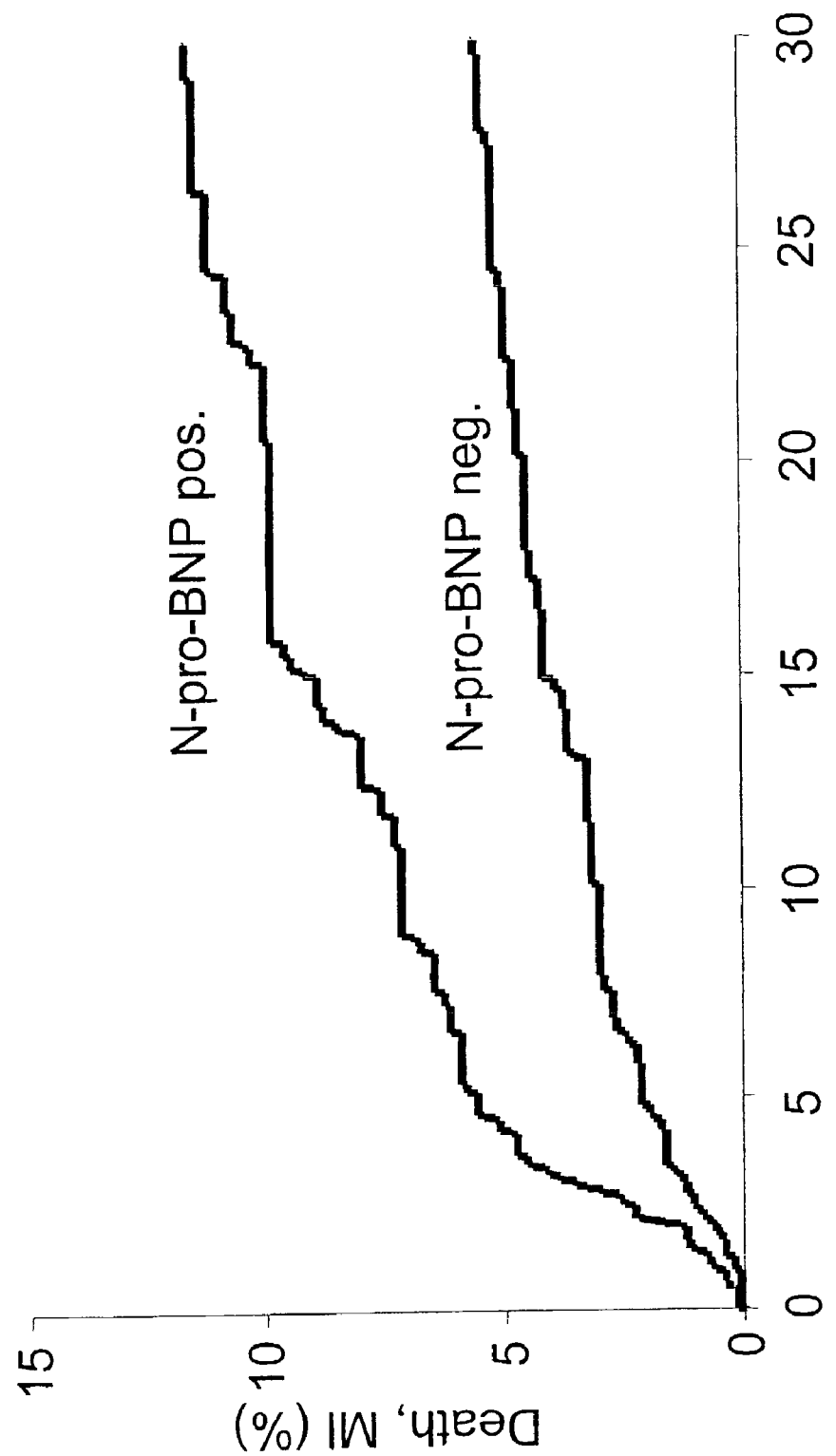
FIG. 2 shows the curve for NT-ProBNP assays carried out on 500 patients with NSTEMI.

FIG. 2 shows the curve for NT-ProBNP

Figure 3:
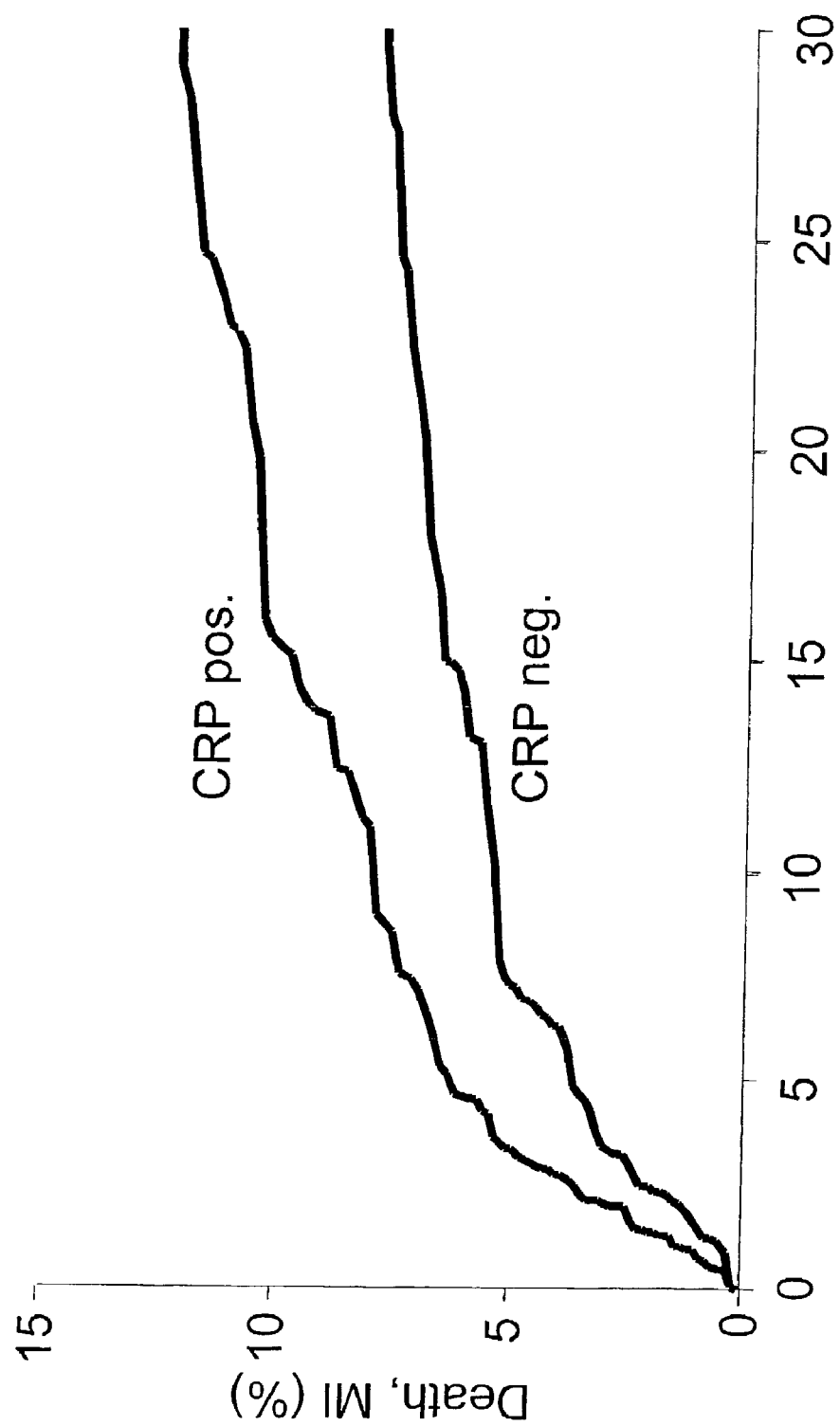
FIG. 3 shows the curve for CRP assays carried out on 500 patients with acute coronary syndrome (NSTEMI).

FIG. 3 shows the curve for CRP.

Additionally, it was determined via a multivariant analysis that the three parameters are independent of each other.

Figure 4:
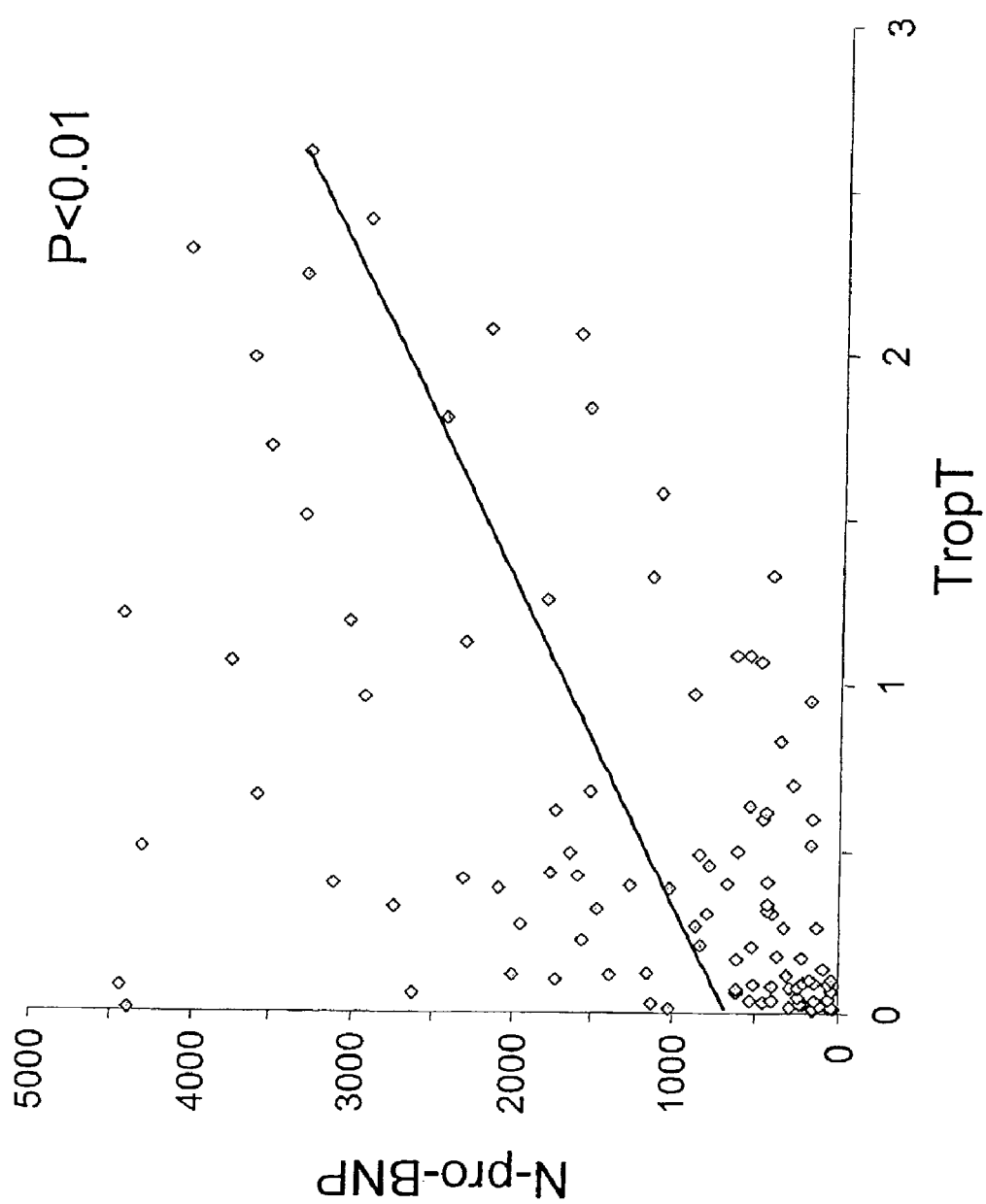
FIG. 4 shows the correlation between the NT-ProBNP value and the troponin T value for 500 patients with NSTEMI.

FIG. 4 shows the correlation between the NT-ProBNP value and the troponin T value. It can be seen that some of the investigated patients have increased values only with regard to one of the parameters.

Example 2

Investigations of the three markers troponin T, NT-ProBNP and CRP were carried out on 1848 patients. The respective ELISA test by Roche was used to determine all three parameters. The results of Example 1 were confirmed. A cut-off value (distinction between positive and negative) of 0.1 pg/l was used for the troponin T test (detection limit 0.01 pg/l). A cut-off value of 400 ng/l was used for the NT-ProBNP test (detection limit 5 ng/l). A cut-off value of 15.0 mg/l was used for the CRP test (detection limit 0.5 mg/l). The NT-ProBNP value is of great importance especially for short-term prognosis, e.g. for the course of the next 72 h.

Figure 5:
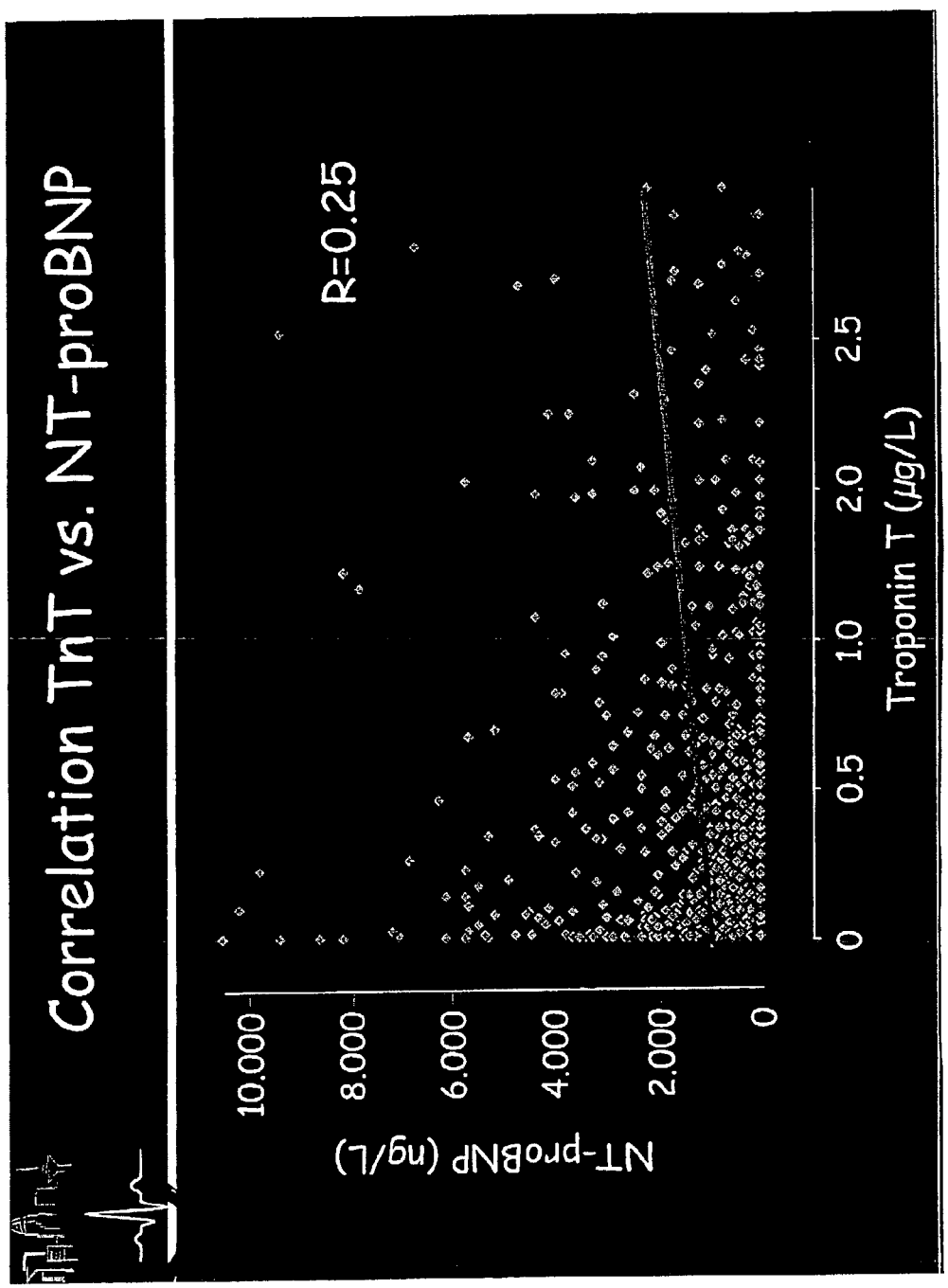
FIG. 5 shows the correlation between the NT-ProBNP value and the troponin T value for 1848 patients.

FIG. 5 shows the correlation between the NT-ProBNP value and the troponin T value.

Figure 6A:
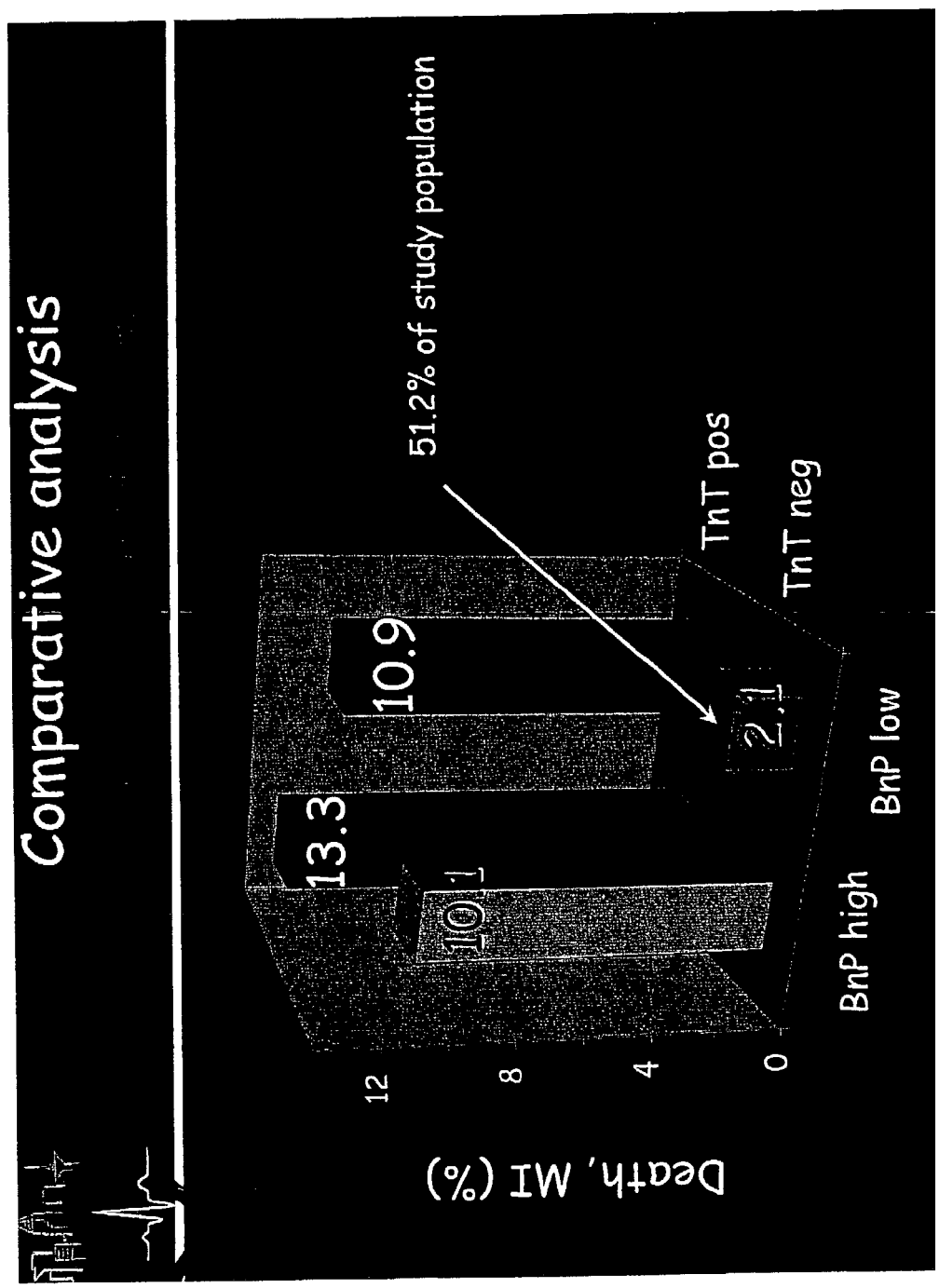
FIG. 6 shows the result of a 30-day follow-up for the part of all patients (a) or of the NSTEMI patients (b) with death or myocardial infarction (MI) with regard to parameters NT-ProBNP and troponin T as well as the combination thereof.
Figure 6B:
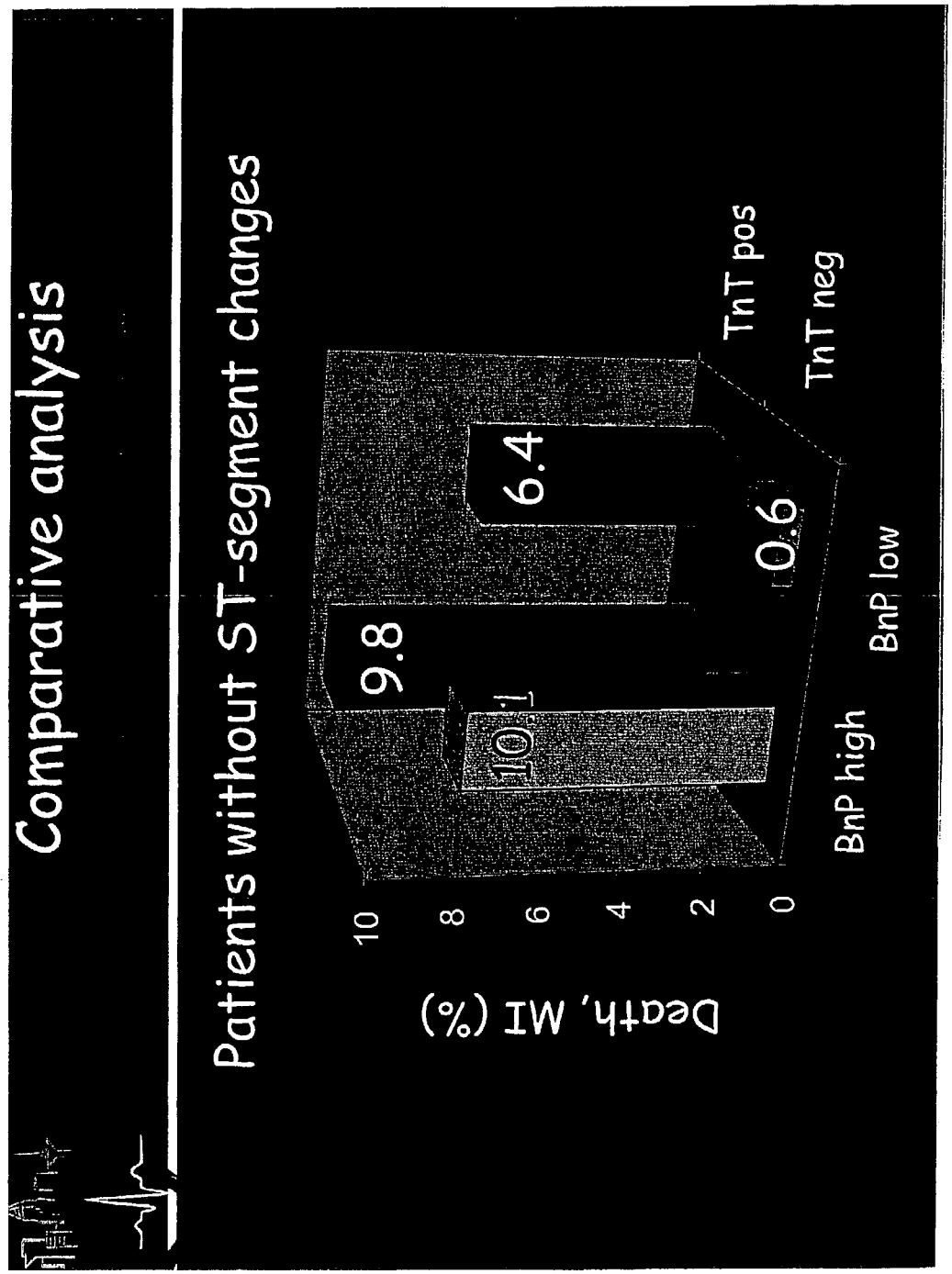

FIG. 6 shows the result of a 30-day follow-up for the part of all patients (a) or of the NSTEMI patients (b) with death or myocardial infarction (MI) with regard to parameters NT-ProBNP and troponin T as well as the combination thereof.

We claim:

1. A method for making a short-term prognosis up to 30 days for a myocardial infarction patient by determining the level of three markers from a sample from the patient, wherein the three markers consist of N-terminal fragment of pro-BNP (NT-ProBNP) marker, at least one ischemic marker selected from the group consisting of troponin T and troponin I, and at least one inflammatory marker selected from the group consisting of C-reactive protein (CRP) and IL-6, comparing the pro-BNP (NT-ProBNP) level, the level of at least one of the ischemic markers and at least one of the inflammatory markers to a control, wherein an elevation of each the pro-BNP (NT-ProBNP), at least one of the ischemic markers, and at least one of the inflammatory markers as compared to the control indicates a less favorable prognosis.

2. The method according to claim 1, wherein the level of the markers are determined in parallel.

3. The method according to claim 1, wherein a single patient sample is used.

4. The method according to claim 1, wherein the presence, quantity, or both presence and quantity of said markers is determined on an automated analyzer.

5. The method according to claim 1, wherein the presence, quantity, or both presence and quantity of said markers is determined using an enzyme immunoassay, an electrochemiluminescence immunoassay, an immunoassay, or a turbidimetric test.

6. The method of claim 1, wherein the short-term prognosis is for the course of 72 hours.

7. The method of claim 1, wherein the short-term prognosis is for the course of 5 days.

8. The method of claim 1, wherein the short-term prognosis is for the course of 10 days.

* * * * *